United States Patent [19]

Marquardt et al.

[11] Patent Number: 5,091,314
[45] Date of Patent: Feb. 25, 1992

[54] CLONING AND USE OF TRANSAMINASE GENE TYRB

[75] Inventors: Rüdiger Marquardt, Frankfurt am Main; Johann Then; Hans-Matthias Deger, both of Hofheim am Taunus; Gerhard Wöhner, Flörsheim am Main, all of Fed. Rep. of Germany; Martyn K. Robinson, Maidenhead; Andrew Doherty, late of Bourne End, both of Great Britain, by Evelyn Leah Kathryn Doherty, legal heir

[73] Assignee: Hoechst Aktiengesellschaft, Frankfurt am Main, Fed. Rep. of Germany

[21] Appl. No.: 566,322

[22] Filed: Aug. 13, 1990

Related U.S. Application Data

[63] Continuation of Ser. No. 98,193, Sep. 17, 1987, abandoned.

[30] Foreign Application Priority Data

Sep. 19, 1986 [DE] Fed. Rep. of Germany ....... 3631829

[51] Int. Cl.$^5$ ............ C12N 1/21; C12N 15/52; C12N 15/70
[52] U.S. Cl. ............ 435/252.33; 435/69.1; 435/71.2; 435/91; 435/108; 435/172.1; 435/172.3; 435/320.1; 435/849; 536/27; 935/6; 935/9; 935/14; 935/22; 935/29; 935/59; 935/60; 935/61; 935/66; 935/73
[58] Field of Search ............ 435/69.1, 71.2, 108, 435/91, 172.1, 172.3, 252.33, 320.1, 849, 108; 536/27; 935/6, 9, 14, 22, 29, 59, 60, 61, 66, 73

[56] References Cited

FOREIGN PATENT DOCUMENTS 0116860 8/1984 European Pat. Off. .

Primary Examiner—Richard C. Peet
Attorney, Agent, or Firm—Finnegan, Henderson, Farabow, Garrett, and Dunner

[57] ABSTRACT

The isolation of the tyrB gene contained in *E. coli* ATCC 11303 and its cloning onto a multicopy plasmid results in a 10-fold increase in the L-phenylalanine yield after the transformation of the starting strain with this plasmid.

2 Claims, No Drawings

CLONING AND USE OF TRANSAMINASE GENE TYRB

This is a continuation of application Ser. No. 07/098,193, filed Sept. 17, 1987 now abandoned.

The last step in the de novo synthesis of phenylalanine comprises the amination of phenylpyruvate by means of a transaminase. Although various transaminases are able to carry out transamination of phenylpyruvate to phenylalanine, this function is performed in the cell mainly by what is called aromatic transaminase. The abbreviation used in genetics for the gene for aromatic transaminase in E. coli is tyrB (Umbarger, Ann. Rev. Biochemistry 47 (1978), 533–606). In the case of E. coli K12, the location of the gene on the "bacterial chromosome" is known accurately, and the gene product has been given the E.C. number 2.6.1.5 (Bachmann et al., Microbiological Reviews 44 (1980), 1–56).

European Patent Application 0,116,860 describes the isolation of the tyrB gene from E. coli K12 and the cloning of this aminotransferase gene onto a multicopy plasmid. The cloned plasmid is transferred back into the strain from which the gene was originally isolated, with the result that the L-phenylalanine production in this strain can be raised by about 11%.

It has now been found, surprisingly, that isolation of the tyrB gene present in E. coli ATCC 11303, and its cloning onto a multicopy plasmid results, after transformation of microorganisms with this plasmid, especially the starting strain, in a 10-fold increase in the yield of L-phenylalanine.

Thus the invention relates to:
1. A replicating extrachromosomal element which contains the tyrB gene isolated from E. coli ATCC 11303.
2. The use of the extrachromosomal element specified under 1) for the synthesis of the aromatic aminotransferase.
3. The use of extrachromosomal elements specified under 1) for the overproduction of L-phenylalanine in microorganisms, which comprises
   a) introduction of the extrachromosomal element into a microorganism,
   b) expression of the tyrB gene in this microorganism, and synthesis of an active aromatic transaminase, and
   c) bringing about the amination of phenylpyruvate by the transaminase.

The invention is explained in detail in the description which follows and defined in the patent claims.

It is possible to use not only the wild type E. coli ATCC 11303 but also its variants and mutants. For example, it is also possible to use a strain which has been mutated by known methods [E. Adelberg et al., Biochem. Biophys. Res. Comm. 18, 788 (1965)] and has been selected for overproduction of L-phenylalanine. The aromatic aminotransferase from E. coli ATCC 11303, for which the tyrB gene codes, inter alia synthesizes L-phenylalanine from phenylpyruvate by transferring an amino group from glutamate. In addition tyrosine, glutamate, aspartate and leucine can be synthesized using the aromatic transaminase. The amino acids isoleucine, valine, leucine, phenylalanine and glutamic acid are formed using a transaminase, which is coded for by the ilvE gene, whereas the amino acids aspartate, glutamate, phenylalanine and tyrosine are synthesized by a transaminase, for whose expression the aspC gene is responsible. However, each of the said transaminases also shows a weak activity in the synthesis of amino acids, which should really be assigned more specifically to one of the other two transaminases.

In order further to increase the synthesis of L-phenylalanine, the tyrB gene, which codes for the aromatic aminotransferase, is cloned. This is achieved by isolating the DNA from E. coli ATCC 11303. Partial digestion of the DNA is followed by the resulting fragments, which have sizes which vary in the range 20–30 kb, being ligated into a cosmid with a replicon which confers a wide host range, and packaging into the heads of phage λ. The cosmid pIMS 6026 is preferably used. The cosmid pIMS 6026 is derived from the cosmid pLAFR 1 (ATCC 37167) by cloning the commercially available EcoRI fragment (Pharmacia, Uppsala, Sweden) on which is located the kanamycin-resistance gene of the transposon Tn 903 into the single EcoRI cleavage site of the cosmid pLAFR 1. It is possible by digestion with Bam HI and subsequent religation to delete most of the EcoRI fragment so that a short piece of DNA remains as an insertion in which a BamHI cleavage site is flanked by 2 EcoRI cleavage sites. This BamHI cleavage site, which is not present on the cosmid pLAFR 1, can be used for cloning. The cosmids are introduced into the microorganism by incubation of the packaged cosmids with an appropriately prepared E. coli DG 30 suspension. E. coli DG 30 has a deficiency of the three transaminases aspC, ilvE and tyrB. Hence, although the strain grows without difficulty on complete medium, for growth on minimal medium various amino acids must be supplied from outside because it cannot synthesize them itself. With appropriate choice of the medium it is possible with the aid of the strain to examine whether a DNA which has been taken up from outside is able to complement the chromosomal defect for a particular transaminase. The introduction of the tyrB gene i$ detected by growth of the E. coli DG 30 on a tyrosine-free minimal medium. Only clones which are able to complement their chromosomal defect for the synthesis of tyrosine by uptake of DNA which contains aspC, tyrB, or ilvE, and originates from the strain E. coli ATCC 11303 are able to grow on this medium. The three transaminases which are coded for by the genes aspC, tyrB and ilvE differ in their substrate specificity, although all three of them are able to form tyrosine.

The aromatic transaminase, which is coded for by the gene tyrB, is unable, for example, to form isoleucine from the keto precursor but is able to synthesize leucine in good yields from the corresponding keto precursor. The transaminase which is coded for by the gene aspC is unable to form isoleucine nor is it efficient in the conversion to leucine.

Accordingly, it is possible to distinguish between the individual clones in respect of the contained transaminase by growth on a minimal medium which is supplemented by the amino acids essential for metabolism apart from one amino acid which is characteristic of the particular gene. Clones of the DG 30 strain which contain the tyrB gene are selected out in this way.

It is now necessary to check whether the clones really do possess the tyrB gene. It is necessary for this to isolate the plasmid DNA from the clones. However, isolation from the strain DG 30 is possible only with difficulty. Although it is possible to obtain plasmid DNA, the yields are only low. Thus, after minilysis, an E. coli strain is transformed with the cosmid DNAs from the clones of interest, from which it is then possible to reisolate the introduced DNA in good yields. E.

coli DH1 (ATCC 33849) is particularly suitable for this purpose.

In the next step, the reisolated cosmid DNA is ligated with a vector of high copy number. It is known from the chromosomal gene map of the strain E. coli K12 that the tyrB gene is located on a ClaI fragment. It is possible that this is also the case in E. coli ATCC 11303. For this reason, the vector which is preferably used is a multicopy plasmid which has a ClaI cleavage site, pAT 153, whose sequence is known, being particularly preferred (Winnacker, E. L., Gene und Klone, (Genes and Clones) VCH-Verlagsgesellschaft, Weinheim).

The cosmid DNA and the vector are completely digested with the restriction enzyme ClaI. The two DNAs are mixed and ligated together, and the product is used to transform competent cells of the host organism in which it is intended to raise the production of phenylalanine. Enterobacteria are preferably used, in particular E. coli, and E. coli ATCC 11303 and its mutants and variants are particularly preferred. Resistant colonies are selected using ampicillin, and tested for insertion on the basis of marker inhibition by replica plating on tetracycline plates. Plasmid DNA is isolated from the appropriate colonies by minilysis, and the presence of ClaI fragments in the vector is checked by complete digestion with the restriction enzyme ClaI. Restriction analysis is carried out to ensure that all the ClaI fragments contained in the original DNA section have been subcloned in this way. Clones which each contain one of these defined ClaI fragments are finally tested, for the activity of the aromatic transaminase, that is to say the gene products of tyrB, using the aspartate-phenylpyruvate aminotransferase (APPAT) assay. It is possible in this way to achieve an increase in the tyrB activity by a factor of 5 to 10. It can be shown, by agarose gel electrophoresis, that the vector of the host strain contains a ClaI fragment about 2.7 MD in size. The invention is described in detail in the examples which follow. Unless otherwise specified, percentage data relate to weight.

EXAMPLE 1

Isolation and digestion of the cosmid pIMS 6026 from E. coli.

The procedure used for the isolation of the cosmid pIMS 6026 from E. coli was either that of Humphreys et al. [Biochim. Biophys. Acta 383, 457-63 (1975)] or an alkaline lysis by the method of Birnboim and Doly [Nucleic Acids Res. 7:151] on a 10 times larger scale. In each case, the plasmid DNA was purified at least once by CsCl/EtBr density gradient centrifugation.

The cosmid pIMS 6026 was completely digested with the restriction enzyme BamHI using the procedure given by the manufacturer, New England Biolabs. To check the completeness of this digestion, an aliquot of the restriction mixture was applied to a 0.8% agarose gel and subjected to electrophoresis. The appearance of only one band after staining with ethidium bromide and irradiation with shortwavelength UV light (254 nm) served to indicate complete digestion. The restriction enzyme was removed from the digested cosmid DNA by treatment with phenol, and the DNA was precipitated with ethanol, washed with 70% strength ethanol, dried in vacuo and then taken up in a suitable volume of TE buffer (10 mM tris; 1 mM EDTA, pH 8.0). A treatment with alkaline phosphatase was then optionally carried out by the method given by the manufacturer, Boehringer Mannheim. After addition of 1 μl of alkaline phosphatase (CIP), the reaction mixture was incubated at 37° C. for 30 minutes and the enzyme was removed by phenol treatment, and the DNA was purified as described above. It was finally resuspended in TE buffer.

EXAMPLE 2

Partial digestion of the DNA from E. coli ATCC 11303

The total DNA from E. coli ATCC 11303 was isolated by the method of Marmur in J. Mol. Biol. 53, 155-162 (1961). The isolated total DNA was partially digested with the restriction enzyme Sau3A so that the resultant fragments were mainly in the size range 20-30kb. Preliminary tests were carried out to establish the optimal ratio of DNA and enzyme for this purpose and the optimal duration of action of the enzyme on the DNA. The appropriate procedure is described in the publication "focus", on page 3 of Vol. 7, No. 2 (1985), which is published by BRL. After the reaction time which had been found to be optimal had elapsed, the enzyme was decomposed by heating at 65° C. for a 10-minute period, and the formation of DNA fragments in the desired size range was checked by agarose gel electrophoresis using suitable DNA markers, for example with phage λ DNA digested with EcoRI.

EXAMPLE 3

Ligation of the restriction mixtures

The total DNA from E. coli ATCC 11303, which had been partially digested with Sau3A, was mixed in a molar ratio of about 1:5 with pIMS 6026 cosmid DNA which had been completely cleaved with BamHI and treated with alkaline phosphatase. The resulting mixture was mixed with a several-fold concentrated buffer as stated by New England Biolabs in such a way that an ionic concentration optimal for the enzyme T4 DNA ligase resulted, and the mixture was incubated with 1 μl of the enzyme at 16° C. for at least 14 hours. The total volume of this mixture was 50 μl with a total DNA concentration of 20 μg/ml.

EXAMPLE 4

Phage λ packaging

The ligase reaction was followed by in vitro packaging of DNA obtained as in Example 3 into phage λ heads. The extracts from two different bacterial strains which are necessary for this purpose can be obtained by the method of Hohn, B., in Wu, R., editor: Recombinant DNA, Methods in Enzymology, Vol. 68, Academic Press, New York, pages 299-309 (1979) or purchased from Boehringer Mannheim or Amersham Buchler, Braunschweig. 3 μl of the mixture obtained as in Example 3 were thoroughly mixed, while cooling in ice, with bacterial extracts supplied by Amersham, which had been thawed immediately beforehand. The mixture was incubated at 20° C. for 30–60 minutes, and then 200 μl of SM buffer (100 mM NaCl, 10 mM MgSO4, 50 mM tris-HCl (pH 7.5), 0.01% gelatin) were added. This mixture was either used directly in a transduction reaction or stored at 4° C., after addition of 10 μl of chloroform, for later use.

EXAMPLE 5

Transduction of E. coli DG 30

0.4% maltose was added to 5 ml of L broth, composed of 1% Bacto Tryptone, 0.5% yeast extract and 0.5% NaCl, and the mixture was inoculated with 50 μl of a liquid culture of E. coli DG 30 in the stationary phase of growth. It was incubated at 37° C. for 12 hours, until the early stationary phase was reached. The bacteria were spun down and carefully resuspended in 2.5 ml of an aqueous solution which was 10 millimolar in MgCl₂. 10 μl of the mixture from Example 4 were mixed with 20 μl of the concentrated bacterial suspension, and the mixture was incubated at room temperature for 50 minutes.

Then 200 μl of L broth were added, and the mixture was incubated at 37° C. for 1 hour, shaking occasionally. 50 μl aliquots of the mixture were plated out on L broth agar which contained 20 μg/ml tetracycline. The plates were incubated at 37° C. for at least 12 hours. With the procedure described, it was possible to obtain a mean of 1,000 colonies from one batch.

EXAMPLE 6

Selection of E. coli DG 30 with an aspC or ilvE or tyrB gene

About 800 colonies, which had been obtained after transduction of E. coli DG 30, by the process described, on L broth agar which contained 20 μg/ml tetracycline, were "picked" onto minimal agar. The minimal agar was composed of M9 medium with glucose (Miller, Experiments in Molecular Genetics, Cold Spring Harbor, 1972) which had been supplemented with the amino acids isoleucine, leucine, valine, aspartic acid and phenylalanine. However, the amino acid tyrosine, which the strain DG 30 is likewise now unable to synthesize, was not added to the medium. Of the 800 "picked" colonies, 7 were able to grow on the minimal medium.

To distinguish the three possible genes aspC, ilvE and tyrB in E. coli DG 30, these 7 colonies were again "picked" onto the abovementioned minimal medium which had been supplemented with the listed amino acids apart from one in each case, for which one of the transaminases which is coded for by one of the genes shows substrate specificity. The result is shown in the table which follows:

| Clone | Minimal medium with supplements apart from | | | | Presumed gene |
|---|---|---|---|---|---|
|  | Asp | Leu | Ile | Tyr |  |
| 1 | + | + | − | + | tyrB |
| 2 | + | + | − | + | tyrB |
| 3 | − | +− | + | +− | ilvE |
| 4 | − | +− | + | +− | ilvE |
| 5 | + | + | − | + | tyrB |
| 6 | + | + | − | + | tyrB |
| 7 | − | +− | + | +− | ilvE |

+ = satisfactory growth
+− = poor growth
− = no growth

EXAMPLE 7

Localization of the tyrB gene

Cosmid DNA was obtained, by minilysis by the method of Maniatis et al., Cold Spring Harbor, pages 366-370 (1982), from clones 1 to 7 which had been obtained as in Example 6. This cosmid DNA was then introduced into E. coli DH1 (ATCC 33849), from which it could be reisolated again in good yields.

Plasmid DNA, which had originally been obtained from clone 5 of E. coli DG 30 (see Example 6), was isolated from the strain E. coli DH1 transformed with this DNA, and was completely digested with the restriction enzyme ClaI, following the instructions of the manufacturer, New England Biolabs. The vector pAT 153 was likewise completely digested with ClaI and was then subjected to a treatment with alkaline phosphatase. The two DNAs were mixed and ligated together in the manner already described in Example 4, and competent cells of the strain E. coli ATCC 11303 were transformed with an aliquot of the ligase mixture, for example 10 μl. Resistant colonies were selected on L broth plates which contained 50 μg/ml ampicillin, and tested by replica plating on L-broth plates with 20 μg/ml tetracycline for marker inactivation and hence insertion. From colonies which exhibited the Ap'Tcˢ phenotype, plasmid DNA was isolated by minilysis, and the presence of ClaI fragments in the vector pAT153 was checked by complete digestion with the restriction enzyme ClaI.

EXAMPLE 8

Examination of the transaminase activity

The clones obtained as in Example 7 were tested, using the APPAT assay (aspartate-phenylpyruvate aminotransferase assay, Sigma test kit G0390, in which o-ketoglutarate was replaced by phenylpyruvate) for the activity of aromatic transaminase, that is to say the gene products of tyrB. The untransformed starting strain E. coli ATCC 11303 was used for comparison. This measurement showed a marked increase in tyrB activity in one case, specifically by a factor of from 5 to 10, compared with the starting strain E. coli ATCC 11303.

It was possible to show, by agarose gel electrophoresis using suitable markers, that the strain which exhibited increased tyrB gene activity contained a pAT 153 vector which contained an incorporated ClaI fragment about 2.7 MD in size. When the isolated plasmid DNA was again used to transform the plasmid-free strain E. coli ATCC 11303, it was possible in every case to observe an increase in the tyrB gene activity by a factor of 5-10. The corresponding plasmid received the designation pIMS 6056.

We claim:

1. A replicating extrachromosomal element containing the tyrB gene, isolated from E. coli ATCC 11303, and a multicopy plasmid.

2. E. coli ATCC 11303, and its variants and mutants, transformed with the extrachromosomal element as claimed in claim 1.